United States Patent [19]
Jarreau et al.

[11] 4,060,607
[45] Nov. 29, 1977

[54] CARDENOLIDE DERIVATIVES

[75] Inventors: François-Xavier Jarreau; Roger Gerard Sarfati, both of Paris, France

[73] Assignee: Etablissements Nativelle S.A., Paris, France

[21] Appl. No.: 684,819

[22] Filed: May 10, 1976

[30] Foreign Application Priority Data
May 16, 1975 France .................. 75.15462

[51] Int. Cl.² .............................. C07J 19/00
[52] U.S. Cl. ..................... 424/241; 260/239.57
[58] Field of Search ..................... 260/239.57

[56] References Cited
U.S. PATENT DOCUMENTS 3,855,208  12/1974  Rutner et al. ............... 260/239.57
3,953,431  4/1976   Rutner et al. ............... 260/239.57

Primary Examiner—Elbert L. Roberts
Attorney, Agent, or Firm—Sughrue, Rothwell, Mion, Zinn and Macpeak

[57] ABSTRACT

Cardiotonic cardenolide derivatives of the formula

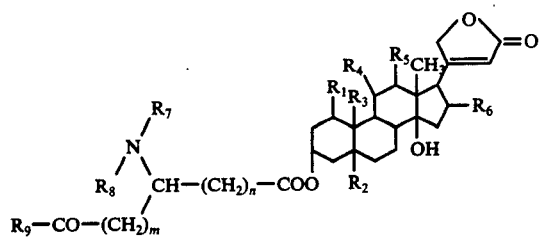

wherein $n$, $m$, $R_1$ to $R_9$ are as hereinafter defined, the mineral or organic salts thereof and a process for their preparation.

9 Claims, No Drawings

CARDENOLIDE DERIVATIVES

BACKGROUND OF THE INVENTION

1. Field of the Invention

The invention relates to novel cardenolide derivatives and their mineral or organic salts, preparation and therapeutic uses.

2. Description of the Prior Art

It is known that numerous natural substances derived from cardiotonic heterosides are used in therapy for the treatment of cardiac insufficiency. The cardiotonic activity of glycoside cardenolides such as digitoxin depends inter alia on the structure of the cardenolide part and the nature of the 3β sugar chain. These natural substances, however, usually have a narrow therapeutic margin and are therefore difficult to use. Consequently it is desirable to prepare compounds having a similar structure and high cardiotonic activity associated with low toxicity. Compounds of this kind can be obtained by grafting a suitable substituent, e.g. an amino radical as described in French Pat. No. 2,181,694, at 3 on the cardenolide part. The amino radical, however, gives basic properties to these compounds.

SUMMARY OF THE INVENTION

The invention relates to cardiotonic cardenolide derivatives having a modified therapeutic effect and amphoteric properties, resulting in special novel pharmacokinetic properties.

The cardenolide derivatives according to the invention can be represented by the following general formula I:

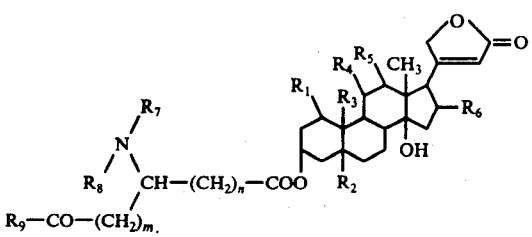
(I)

in which $n$ and $m$ are the same or different and can be equal to 0, 1, 2, 3, or 4; $R_1$, $R_2$, $R_4$, $R_5$, and $R_6$ are the same or different and denote a hydrogen atom or a hydroxy, alkoxy or acyloxy group; $R_3$ denotes a lower alkyl, aldehyde, halo-alkyl, hydroxyalkyl, acyloxyalkyl or ethylene dioxyalkyl group; $R_7$ denotes a hydrogen atom or an alkyl, acyl, alkyloxycarbonyl or aralkoxycarbonyl group; $R_8$ denotes a hydrogen atom or an alkyl group; $R_7$ and $R_8$ can form a heterocyclic ring together with the nitrogen atom; $R_9$ denotes a hydroxy, alkoxy, or aralkoxy group or an amino radical of an amino-acid or oligo-peptide.

In formula I above, $n$ is preferably 1 to 2 and $m$ is 0, or vice versa. When $R_7$ denotes an acyl group, the group can e.g. be an acetyl group or an acyl group derived from an amino-acid or oligo-peptide; the alkyloxy-or aralkoxy-carbonyl group can e.g. be a t-butyloxycarbonyl or benzyloxycarbonyl group variously substituted at the aromatic ring; $R_7$ and $R_8$ can together be two acyl radicals and form a phthalimide group with the nitrogen atom; and $R_9$ can denote a hydroxy group or an alkoxy group such as methoxy, ethoxy, or phthalimidomethyloxy, or an aralkoxy group, inter alia a benzyloxy group.

As already stated, the cardiotonic effect of compounds such as those represented by formula I depends inter alia on the structure of the cardenolide part, more particularly on the stereochemistry of the substituents grafted thereon. The invention preferably relates to the cardenolide derivatives represented by formula Ia hereinafter, where the stereochemical configuration has been shown.

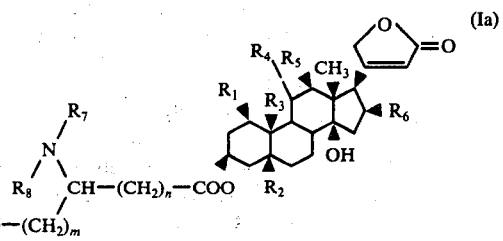
(Ia)

The invention also relates to a method of preparing the formula I compounds by coupling the cardiotonic genins via the 3-alcohol group, preferably the 3β - alcohol group, and the amino diacids via one or the other carboxylic acid group.

DETAIL DESCRIPTION OF THE INVENTION

According to the invention, a previously-protected cardenolide is reacted with an amino diacid derivative which has been suitably substituted at the amino group and at one of the two carboxylic acid groups, the other being suitably activated. The starting cardenolide can be e.g. digitoxigenin, digoxigenin, strophanthidin, gitoxigenin, gitaloxigenin, ouabaigenin, etc. The following are examples of amino diacids which can be used for preparing the compounds according to the invention: aspartic acid, glutamic acid, 2-amino propane-1,3-dioic acid, etc., in the laevo, dextro or racemic form. If required, these amino diacids can be substituted at the nitrogen atom.

The groups protecting the amino radical and the carboxylic acid group can be those commonly used in peptide synthesis, e.g. the benzyloxycarbonyl, trityl, phthalimido groups, etc. for the amino radical and the benzyl or methyl ester or phthalimidomethyl groups, etc. for the carboxylic acid group.

The second carboxylic acid group can be activated by the conventional methods of peptide synthesis, e.g. by converting it into acyl chloride, active ester, anhydride, etc., or associating it with a condensation agent such as dicyclohexyl-carbo-diimide, N-ethyl-5-phenyl-3'-isoxazolium sulphonate, or tetraethyl pyrophosphite.

Furthermore, the groups protecting the various alcohol, carboxylic acid, amine and/or aldehyde groups can be eliminated from the condensation products and replaced if required by other groups, using conventional methods.

Preferably, coupling is brought about by adding the cardenolide when cold to a solution of suitably protected, activated acid and by letting the reaction proceed at ambient temperature for a few hours. The main substance produced is a compound which is extracted with an organic solvent, after the reaction medium has been diluted with water and acidified, and is purified by crystallization or chromatography.

The compounds according to the invention represented by formula I hereinbefore have a cardiotonic effect which is rather different from that of known cardiotonic heterosides.

More particularly, cardenolide derivatives according to the invention have important pharmacological properties, e.g. an inhibiting effect on the membranous ATPase, checked on the brain tissue, and a convulsing effect after injection into the lateral ventricle of the rat's brain by the method of E. P. Noble, J. Axelrod and R. J. Wurtman described in "Life Science" (1967, 6, 281).

The inotropic activity which varies for different species, was tested on the isolated guinea-pig heart (Langendorff type) and the dog's heart in situ. The chronotropic activity was tested on the same preparations. In some cases, a dissociation of the pharmacological parameters was observed so that cardenolide derivatives according to the invention differ from conventional cardiotonic heterosides usually used in therapy.

The active doses, when intravenously administered to the dog, are considerably lower than 1 mg per kg weight, which means that these products are at approximately the same level as natural digitalis substances, though they have a different therapeutic margin.

It is particularly noteworthy that the inhibiting effect of the compounds according to the invention on the membranous ATPase is always found to persist, whereas there are marked variations in the inotropic effect, depending on the substituents grafted at 3 on the cardenolide part, and depending on the nature of the cardenolide itself.

The compounds according to the invention are particularly suitable for the treatment of cardiac insufficiency and irregularities in the rhythm.

The compounds according to the invention can be administered in conventional forms. They can be orally administered in pills, capsules or tablets containing one or more compounds according to the invention associated with conventional pharmaceutically acceptable excipients such as lactose, starch, polyvinylpyrrolidone, magnesium stearate, powdered cellulose, talcum etc. The compounds can be parenterally administered using hydro-alcoholic solutions, twice-distilled water or propylene glycol or a mixture of these various solvents.

All formulations suitable for these methods of administration can be used, the drug being associated, as the active principle, with a pharmaceutically acceptable excipient in the usual manner.

The following examples non-limitatively illustrate the invention.

EXAMPLE 1

Preparation of 3$\beta$-($\alpha$-L-aspartyl) Digitoxigenin and a. 3 $\beta$-[$\alpha$-N-benzyloxycarbonyl-$\beta$-benzyl)-L-aspartyl]; digitoxigenin 15 cm$^3$ of a molar solution of benzene sulphonyl chloride in pyridine were added with agitation at $-5°$ C to 5.358 g of N-benzyloxycarbonyl-$\beta$-benzyl L-aspartic acid in solution in 30 cm$^3$ anhydrous pyridine. Agitation at $-5°$ C was continued for 30 minutes, after which 2.808 g of digitoxigenin in solution in 20 cm$^3$ anhydrous pyridine were added in 30 minutes. Agitation was continued at $-5°$ C for 45 minutes, at 0° C for 2 hours and at room temperature for 48 hours.

Next, the medium was flooded and acidified to pH 2-3 by a solution of 10% citric acid in water, then extracted with ethyl acetate. The extract was washed in water and then in sodium bicarbonate solution and finally in water, and dried and distilled to dryness, yielding 7.422 g of residue. The residue was crystallized in ethanol at 95° and, after recrystallization, yielded 3.88 dg of white crystals giving a single spot in thin-layer chromatography (Merck G silica gel CH$_2$Cl$_2$-MeOH 97-3) consisting of 3$\beta$-[$\alpha$-N-benzyl-oxycarbonyl-$\beta$-benzyl)-L-aspartyl] digitoxigenin. Yield $\simeq$75%.

Melting point (Kofler) 177°–178° C

I.R. spectrum (Nujol) 3465, 3410, 1755, 1739, 1722 cm$^{-1}$

N.M.R. spectrum (CDCl$_3$)$\delta$ = 51 and 54 (2 s, CH$_3$), 290 (2H), 304 (s, 5H), 347 (1H) 438 (s 10H) cps.

b. 3 $\beta$-($\alpha$-L-aspartyl)digitoxigenin 3.570 g of 3$\beta$-[$\alpha$-(N-benzyloxycarbonyl-$\beta$- benzyl)-L-aspartyl] digitoxigenin was dissolved in 750 cm$^3$ of methanol and agitated for 3 hours in a hydrogen atmosphere in the presence of 900 mg of 5% palladium on calicum carbonate. The medium was filtered and concentrated to dryness, yielding 2.43 g of residue. The residue was crystallized from ethanol at 90° C and yielded 1.84 g of 3 $\beta$-($\alpha$-L-aspartyl) digitoxigenin (yield $\simeq$ 75%).

T.L.C. : silica gel G plate — CHCL$_3$ solvent saturated with a mixture of EtOH/NH$_3$OH (40/15)

Melting point: (Kofler) (decomposition): 220°–240° C

I.R. spectrum (Nujol): 3490, 1745 cm$^{-1}$

N.M.R. spectrum (DMSO d$_6$): $\delta$=(cps)46 and 51 (2 s, CH$_3$), 293 (2H), 351 (1H)

c. 3$\beta$-[$\alpha$-(N-acetyl)-L-aspartyl]digitoxigenin 400 mg of 3$\beta$-($\alpha$-L-aspartyl) digitoxigenin in solution in 15 cm$^3$ anhydrous methanol with 4 cm$^3$ acetic anhydride was left at ambient temperatuer for 4 hours.

The medium was distilled to dryness, yielding 447 mg of residue. The residue was dissolved in 10 cm$^3$ methylene chloride and extracted with an aqueous solution of sodium bicarbonate. The alkaline extract was acidified to pH 2 and re-extracted with methylene chloride. After being washed, dried and distilled to dryness, the substance yields 294 mg of 3$\beta$-[$\alpha$-(N-acetyl)-L-aspartyl] digitoxigenin, a white residue giving a single spot in T.L.C. (Merck G silica gel, CHCl$_3$ saturated with a mixture of EtOH—NH$_4$OH(40-15).

I.R. spectrum (Nujol): 3340, 1740 cm$^{-1}$

N.M.R. (CDCl$_3$): $\delta$=(cps) 53, 55 and 122 (3 s, CH$_3$) 292 (2H), 306, (1H), 350 (OH), 410 (NH)

d. 3$\beta$-[$\alpha$-(N-acetyl-$\beta$-methyl)-L-aspartyl] digitoxigenin 2 mM of diazomethane in solution in ether were added at 0° C and with agitation to 150 mg of 3$\beta$-[$\alpha$-(N-acetyl)-L-aspartyl]digitoxigenin in solution in 2 cm$^3$ methanol and 3 cm$^3$ ether. After 30 minutes agitation at 0° C, the medium was distilled to dryness and yielded 153 mg of 3$\beta$-[$\alpha$-(N-acetyl-$\beta$-methyl)-L-aspartyl] digitoxigenin, giving a single spot in T.L.C. (merck G silica gel, CH$_2$Cl$_2$(MeOH 9/1).

I.R. spectrum (Nujol): 3390, 1740 cm$^{-1}$

N.M.R. spectrum (CDCl$_3$)$\delta$ =(cps) 52, 57, 121 and 219 (4 s, CH$_3$), 173 (2H), 291 (2H), 307 (1H), 349 (1H) 399 (d, 1H).

Mass spectrum: M$^+$ = 545 (C$_{30}$H$_{43}$NO$_8$)

EXAMPLE 2

Preparation of 3β-(β-L-aspartyl) Digitoxigenin and Derivatives a.

3β-[β-(N-benzyloxycarbonyl-α-p--nitrobenzyl)-L-aspartyl] digitoxigenin

As in Example 1 (a), 281 mg digitoxigenin in solution in 5 cm³ pyridine was coupled with 603 mg of -(N-benzyloxycarbonyl-α-p-nitrobenzyl) L-aspartic acid in the presence of 260 milligrams benzenesulphonyl chloride in 6 cm³ pyridine.

After agitation for 48 hours, the reaction medium was acidified to pH 2-3 with a solution of 10% citric acid and extracted with ethyl acetate. The extract, distilled to dryness, yielded 780 mg of a yellow-orange residue which was chromatographed on 60 g Merck silica. The fractions, when eluted with a mixture of 98.5/1.5 methylene chloride/methanol, yielded 530 mg of pale yellow, still impure, residue. A second chromatographic oeration on 10 g silica yielded 390 mg of 3β-[β-(N-benzyloxycarbonyl-α-p-nitrobenzyl)-L-aspartyl] digitoxigenin (yield = 70%).

I.R. spectrum (Nujol): 3440, 1740 cm$^{-1}$

N.M.R. spectrum (CDCl₃): δ=(cps)51 and 55 (2s. CH₃), 177 (2H), 236 (1H), ; 291 (2H), 306 and 314 (2 s, CH₂), 350 (2H), from 438 to 486 (s and 2d, Ar).

3β-[β-(N-benzyloxycarbonyl)-L-aspartyl] digitoxigenin 1 g of 3β-[β-(N-benzyloxycarbonyl-α-p-nitrobenzyl)-L-aspartyl] digitoxigenin was hydrogenated in the presence of 250 g of 5% palladium on calcium carbonate in 150 cm³ methanol for 1½ hours and, after filtration and evaporation to dryness, yielded 901 mg of yellow-oranfge residue. The residue was dissolved in methylene chloride and extracted with sodium bicarbonate solution. The alkaline extract was washed with methylene chloride and acidified to pH 2 with concentrated HCl amd re-extracted with methylene chloride to dryness, yielding 680 mg of 3 β-[β-(N-benzyloxycarbonyl)-L-aspartyl] digitoxigenin (yield = 83%).

I.R. spectrum (Nujol): 3425, 1728 cm$^{-1}$
N.M.R. spectrum (CDCl₃): δ=(cps) 51 and 55 (2 s, CH₃) 175, 291, 303, 349, 373 (OH), 432 (HR).

c. 3β —(β-L-aspartyl)digitoxigenin 600 mg of 3β-[β-(N-benzyloxycarbonyl)-L-aspartyl] digitoxigenin was placed in a hydrogen atmosphere in the presence of 150 mg of 5% palladium on calcium carbonate in 90 cm³ methanol. After 2 hours the medium was filtered and distilled to dryness, yieling 483 mg of residue. The residue was crystallized from the methanol/ethyl acetate mixture and then from methanol, yielding 253 mg of pure crystals of 3(1β-β-L-aspartyl)digitoxigenin (yield = 54%).

Melting point = decomposition at approx. 260° C.
I.R. spectrum (Nujol): 3625, 3160, 1745, 1715 cm$^{-1}$
N.M.R. spectrum (CH₃OD): δ=(cps)52, 58 (2 s CH₃), 177 (2H), 233 (1H), 297 (2H) 351 (1H).

d. β -[β-(N-acetyl-α-methyl)-L-asparty)] digitoxigenin

In the same mannr as in Example 1(c), acetic anhydride was reacted at ambient temperature with 3β-[β -L-aspartyl]digitoxigenin in methanol. Next, as in Example 1 (d), the product was treated with diazomethane in solution in either at 0° C, to obtain 3 β -[β-(N-acetyl-α -methyl)-L-aspartyl]digitoxigenin.

N.M.R. spectrum (CDCl₃): δ =(cps) 51, 52, 121 and 224 (4 s, CH₃) 174 (q. 2H), 293 (3H), 306 (1H), 350 (s, 1H), 398 (d, 1H)
Mass spectrum: M+ =545 (C₃₀H₄₃NO₈)

EXAMPLE 3

Preparation of 3β-(α-L-glutamyl)digitoxigenin and derivatives thereof a.

3β-[α-(N-benzyloxycarbonyl-γ-benzyl)-L-glutamyl]-digitoxigenin

In the same manner as in example 1 (a), 1 g of F digitoxigenin in solution in 8 cm³ pyridine was added to a cooled mixture of 2 g N-benzyloxycarbonyl-γ-benzyl-L-glutamic acid and 0/930 g benzenesulphonyl chloride in 15 cm³ pyridine. After agitation for 20 hours, the reaction medium was acidified to pH 2—3 with a solution of 10% citric acid, then extracted with ethyl acetate. The extract, distilled to dryness, yielded a 2.8 g residue which was chromatographed on a column of 75 g Merck silica gel.

The fractions, when eluted witha 99/1 mixture of methylene chloride and methanol, yilded 1.5 g of 3β-[α-(N-benzyloxycarbonyl-γ-benzyl-L-benzyl)-glutamyl]-digitoxigenin (80% yield), a white powder giving a spot in T.L.C. (Merck G silica gel — CH₂Cl₂/MeOH 95/5).

I.R. spectrum (Nujol); 3510, 3340, 1735 cm$^{-1}$
N.M.R. spctrum (CDCL₃): δ = (cps) 50 and 54 (2 s, CH₃) 264 (1H) 290, (2H), 303(s, 4H) 328 (NH) 348 (1H), 436 (s, Ar).

b. 3β-(α -L-glutamyl)digitoxigenin 1.4 grams of 3β-[α-(N-benzyloxycarbonyl-γ-benzyl)-L-glutamyl] digitoxigenin was hydrolyzed in the presence of 350 mg of 5% palladium/calcium carbonate in 200 ml methanol for 90 minutes and, after filtration and evaporation to dryness, yielded 970 mg of residue. The residue was crystallized from methano/ethyl acetate, yielding 470 mg of pure crystals of 3β-(α-L-glutamyl) digitoxigenin (yield: 50%).

Melting point 264° C (decomposition)
I.R. spectrum (Nujol): 3560, 3430, 1745 cm$^{-1}$
N.M.R. spectrum (DMSOd₆): δ=(cps) 46, 54 (2 s, CH₃), 280 (OH, NH₂), 295 (3H), 353 (1H).

c. 3β-[α-(N-acetyl-γ-methyl)-L-glutamyl] digitoxigenin

As in Example 1 (c), acetic anhydride was reacted at room temperature with 3β-(α-L-glutamyl) digitoxigenin in methanol. The product was then treated as in Example 1 (d) with diazomethane in solution in ether at 0° C, thus obtaining 3β-[α-(N-acetyl-γ-methyl)-L-glutamyl] digitoxigenin.

N.M.R. spectrum (CDCl₃): δ = (cps) 52, 53 120 and 219 (4 s, CH₃), 170 (1H), 272 (1H), 293 (2H), 303 (1H), 350 (1H), 378 (d, NH).
Mass spectrum M+ = 559 (C₃₁H₄₅NO₈).

EXAMPLE 4

Preparation of 3β-(α-L-aspartyl) digoxigenin and derivatives a. 3β-[α-(N-benzyloxycarbonyl-β-benzyl)-L-aspartyl]-12β-acetyl digoxigenin

As before, 714 mg of N-benzyloxycarbonyl-β-benzyl L-aspartic acid, 350 mg benzenesulphonyl chloride and 432 mg 12β-acetyl digoxigenin were left under agitation in solution in 8 cm³ of cooled pyridine for 6 hours.

The reaction medium was then acidified to pH 2-3 with a 10% solution of citric acid, then extracted with ethyl acetate. The extract yielded 982 mg of residue, which was chromatographed on a column of 25 g Merck silica. The fractions eluted with a 99/1 mixture of methylene chloride and methanol yielded 490 mg of 3β-[α-(N-benzyloxycarbonyl-β-benzyl)-L-aspartyl]-;b 12β-acetyl digoxigenin, yielding a single spot (yield = 63%).

I.R. spectrum (Nujol): 3440 and 1732 cm⁻¹
N.M.R. spectrum (CDCl₃)δ (cps) 53, 53.5 and 129 (3s, CH₃) 172 (3H), 275 (2H), 289 (2H), 304 (5H), 343.5 (NH), 348 (1H) and 437 (10 H).

b. 3β-(α-L-aspartyl)-12β-acetyl digoxigenin

As before, 500 mg of 3β-[α-(N-benzyloxycarbonyl-β-benzyl)-L-aspartyl]-12β-acetyl digoxigenin in 75 cm⁻³ methanol were left in a hydrogen atmosphere under agitation in the presence of 125 mg of 5% palladium on calcium carbonate for 3 hours. After filtration, evaporation and washing the yellow residue in ether, the yield was 264 mg of 3β-(α-L-aspartyl)-12β-acetyl digoxigenin, single spot in T.L.C. (yield:≃75%).

I.R. spectrum (Nujol): 3440 and 1735 cm−1.
N.M.R. spectrum (CD₃OD): δ (cps) 54, 59.5 and 124.5 (3 S, CH₃), 170 (3H),243 (1H), 275 (1H) 310 (1H), 350 (2h).

(.3β-[α-(N-benzyloxycarbonyl)-L-aspartyl] digoxigenin 70 cm³ of water containing 1.34 g potassium bicarbonate and 70 mg potassium carbonate were added dropwise to 700 mg of 3β-[α-(N-benzyloxycarbonyl-β-benzyl)-L-aspartyl]-12β-acetyl digoxigenin in solution in 70 cm³ of ethanol at 95° C.

The medium was left for 12 days in a closed vessel in an oven at 50°, then concentrated to a third of its volume, extracted three times with methylene chloride, acidified to pH 2 with hydrochloric acid and finally extracted with an 8/2 mixture of chloroform and ethanol.

The extract, after being washed, dried and distilled to dryness, yielded 546 mg of pure 3β-[α-(N-benzyloxycarbonyl)-L-aspartyl] digoxigenin (yield = 94%).

I.R. spectrum (Nujol): 3420 and 1730 cm−1
N.M.R. spectrum (C₅D₅N): δ=(cps)52 and 72 (2 s, CH₃) 199 (2H), 220 (2H), 307 (2H), 316.5 (3H), 436.5 (Ar).

d. 3β-(α-L-aspartyl) digoxigenin 480 mg of 3β-[α-(N-benzyloxycarbonyl)-L-aspartyl] digoxigenin was hydrolyzed in solution in 70 cm³ methanol in the presence of 120 mg of 5% palladium on calcium carbonate for 5 hours. The yield after filtration and evaporation was 376 mg of 3β-(α-L-aspartyl) digoxigenin (yield ≃ 100%).

I.R. spectrum (Nujol): 3400, 3360, 1740 cm−1
N.M.R. spectrum (CD₃OD): δ= (cps) 46.5 and 58 (2 s, CH₃) 168 (2H), 246 (1H), 309 (1H), 351 (1H).

Of course, the invention is not limited to the compounds represented by the general formula (I), but also extends to their salts, more particularly their pharmaceutically acceptable salts. Note that, in the presence of an amino —NR₇R₈ group and an acid R₉CO group, R₉ being inter alia a hydroxy group, salts can be prepared by action either of bases or of mineral or organic acids.

What we claim is:

1. Cardenolide derivatives having the general formula:

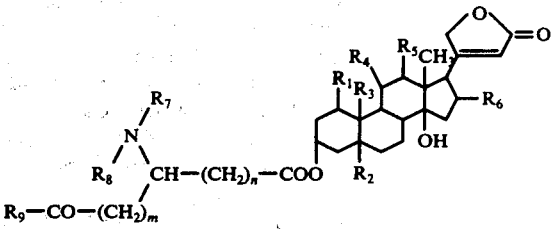

in which n and m are the same or different and can be equal to 0, 1, 2, 3 or 4; R₁, R₂, R₄, R₅, and R₆ are the same or different and denote a hydrogen atom or a hydroxy, alkoxy or acyloxy group; R₃ denotes a lower alkyl, aldehyde, halo-alkyl, hydroxyalkyl, acyloxyalkyl or ethylene dioxyalkyl group; R₇ denotes an hydrogen atom or an alkyl, alkyloxycarbonyl or aralkoxycarbonyl group; R₈ denotes a hydrogen atom or an alkyl group; R₉ denotes a hydroxy, alkoxy or aralkoxy group; and pharmaceutically acceptable mineral or organic salts of the aforementioned derivatives.

2. Cardenolide derivatives according to claim 1, characterized in that n or m is equal to 0.

3. 3β-[α- or [β-L-aspartyl]digitoxigenin and pharmaceutically acceptable mineral or organic salts thereof.

4. 3β-(α-L-glutamyl) digitoxigenin and pharmaceutically acceptable mineral or organic salts thereof.

5. 3β-[α- or [β-(N-acetyl)-L-aspartyl] digitoxigenin and pharmaceutically acceptable mineral or organic salts thereof.

6. 3β-[α-(N-acetyl-β-methyl)-L-aspartyl] digitoxigenin and pharmaceutically acceptable mineral or organic salts thereof.

7. 3β-(α-L-aspartyl) digoxigenin and pharmaceutically acceptable mineral or organic salts thereof.

8. Method for treating cardiac insufficiency and rhythm irregularities comprising orally or parenterally administering a therapeutically effective amount of a cardenolide derivative as described in claim 1, together with a pharmaceutically acceptable carrier.

9. Cardenolide derivatives having the general formula

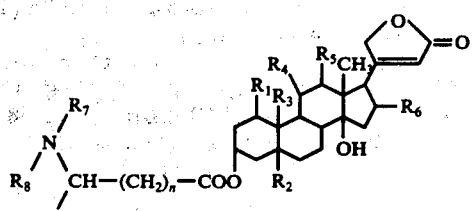

in which n and m are the same or different and can be equal to 0, 1, 2, 3 or 4; wherein R₁, R₂ and R₅ denote a hydrogen atom or a hydroxy group; $R_3$ denotes a lower alkyl, aldehyde or hydroxyalkyl group; $R_4$ denotes a hydrogen atom; and $R_6$ denotes a hydrogen atom, a hydroxy, alkoxy, or acyloxy group; $R_7$ denotes an hydrogen atom or an alkyl, alkyloxycarbonyl or aralkoxycarbonyl group; $R_8$ denotes a hydrogen atom or an alkyl group; $R_9$ denotes a hydroxy, alkoxy or aralkoxy group; and pharmaceutically acceptable mineral or organic salts of the aforementioned derivatives.

* * * * *